US012496424B1

(12) United States Patent
Natrillo et al.

(10) Patent No.: US 12,496,424 B1
(45) Date of Patent: Dec. 16, 2025

(54) NONINVASIVE WEARABLE DEVICE FOR REMOTE VITAL SIGN MONITORING AND AUTONOMIC NERVOUS SYSTEM REGULATION USING VIBRATORY AND AUDITORY STIMULATION

(71) Applicants: Richard A. Natrillo, Boca Raton, FL (US); Arieh S. Halpern, Beverly Hills, CA (US); Stephen W. Porges, Atlantic Beach, FL (US); Gregory F. Lewis, Bloomington, IN (US)

(72) Inventors: Richard A. Natrillo, Boca Raton, FL (US); Arieh S. Halpern, Beverly Hills, CA (US); Stephen W. Porges, Atlantic Beach, FL (US); Gregory F. Lewis, Bloomington, IN (US)

( * ) Notice: Subject to any disclaimer, the term of this patent is extended or adjusted under 35 U.S.C. 154(b) by 0 days.

(21) Appl. No.: 18/999,614

(22) Filed: Dec. 23, 2024

Related U.S. Application Data

(60) Provisional application No. 63/660,194, filed on Jun. 14, 2024.

(51) Int. Cl.
*A61M 21/00* (2006.01)

(52) U.S. Cl.
CPC ..... *A61M 21/00* (2013.01); *A61M 2021/0022* (2013.01); *A61M 2021/0027* (2013.01)

(58) Field of Classification Search
CPC .......... A61M 21/00; A61M 2021/0022; A61M 2021/0027
See application file for complete search history.

(56) References Cited

U.S. PATENT DOCUMENTS

| | | | |
|---|---|---|---|
| 10,702,154 B2 | 7/2020 | Porges | |
| 11,134,844 B2 | 10/2021 | Porges | |
| 11,684,540 B2 | 6/2023 | Harper et al. | |
| 2022/0362095 A1* | 11/2022 | Rabin | A61H 19/30 |
| 2023/0277411 A1 | 9/2023 | Harper et al. | |

* cited by examiner

*Primary Examiner* — Carrie R Dorna
*Assistant Examiner* — Joshua Daryl D Lannu
(74) *Attorney, Agent, or Firm* — Venable LLP; Ryan T. Ward

(57) ABSTRACT

Systems, methods, and computer-readable storage media for a wearable medical device, and more specifically to a wearable medical device for (a) regulating and augmenting the autonomic nervous system (ANS) through vibratory and auditory stimuli to improve health and cognitive states in individuals under stress and (b) for use in remote vital sign monitoring of the wearer. The wearable device captures physiological data, such as heart rate and heart rate variability, and based on that physiological data estimates the user's current state. The wearable device can then communicate that current user state to the user via a smartphone or other user interface.

20 Claims, 7 Drawing Sheets

Wearable Wrist Monitor / Communicator

NONINVASIVE WEARABLE DEVICE FOR REMOTE VITAL SIGN MONITORING AND AUTONOMIC NERVOUS SYSTEM REGULATION USING VIBRATORY AND AUDITORY STIMULATION

PRIORITY

This application claims priority to U.S. provisional patent application No. 63/660,194, filed Jun. 14, 2024, the contents of which are incorporated herein in their entirety.

BACKGROUND

1. Technical Field

The present disclosure relates to a wearable medical device, and more specifically to a wearable medical device for (a) regulating and augmenting the autonomic nervous system (ANS) through vibratory and auditory stimuli to improve health and cognitive states in individuals under stress and (b) for use in remote vital sign monitoring of the wearer.

2. Introduction

The autonomic nervous system (ANS) plays a crucial role in regulating physiological functions and maintaining homeostasis. Dysregulation of the ANS can lead to various health issues, including stress, anxiety, and impaired cognitive function. Current solutions for ANS regulation are limited in their ability to provide personalized, noninvasive interventions. For example, vagal nerve stimulation (VNS) has been implemented to optimize bio-behavioral state and general wellbeing. However, such implementation fails to be individualized while also being overly invasive.

SUMMARY

Additional features and advantages of the disclosure will be set forth in the description that follows, and in part will be understood from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed are systems, methods, and non-transitory computer-readable storage media which provide a technical solution to the technical problem described. A system configured to perform the concepts disclosed herein can include: at least one physiological sensor configured to measure heart rate and heart rate variability (HRV) of a person; at least one accelerometer; at least one emitter; at least one processor; a non-transitory computer-readable storage medium with instructions that, when executed by the at least one processor, cause the at least one processor to: receive measurements from the at least one physiological sensor and the at least one accelerometer; execute a trained model based on the measurements, wherein input to the trained model comprises the measurements and output of the trained model comprises a current user state; and causing the at least one emitter to generate output based on the current user state, the output comprising at least one of vibrational output or acoustic output.

A method for practicing the concepts disclosed herein can include: receiving, at a computer system from at least one physiological sensor and from at least one accelerometer, measurements of a user, the at least one physiological sensor and the at least one accelerometer embedded within a neck band worn by the user; executing, via at least one processor of the computer system, a trained model, wherein inputs to the trained model comprise the measurements, and wherein output of the trained model comprise a current user state; and displaying, via a user interface of the computer system, the current user state.

A non-transitory computer-readable storage medium configured as disclosed herein can have instructions stored which, when executed by at least one processor, cause the at least one processor to perform operations which include: receiving, from at least one physiological sensor and from at least one accelerometer, measurements of a user, the at least one physiological sensor and the at least one accelerometer embedded within a neck band worn by the user; executing a trained model, wherein inputs to the trained model comprise the measurements, and wherein output of the trained model comprise a current user state; and causing display, via a user interface, of the current user state.

DETAILED DESCRIPTION

Figure 1:
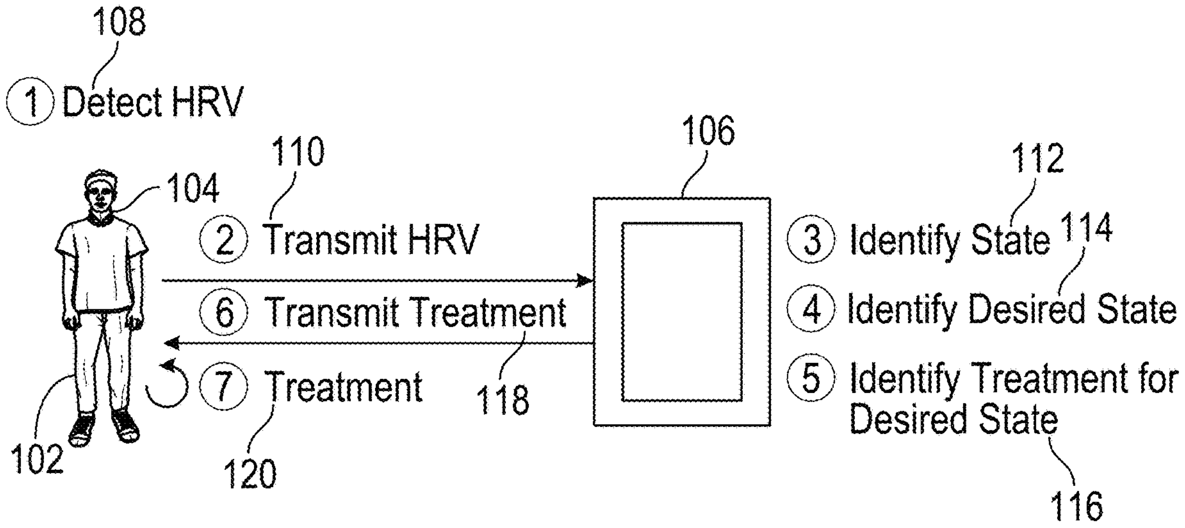
FIG. 1 illustrates an example system with a user wearing a wearable device in wireless communication with a mobile communication device.

Various embodiments of the disclosure are described in detail below. While specific implementations are described, this is done for illustration purposes only. Other components and configurations may be used without parting from the spirit and scope of the disclosure.

Systems configured as disclosed herein monitor the ANS through continuous monitoring of different aspects of the human body. Non-limiting monitoring can include electrocardiogram (ECG) monitoring, pulse wave topography, oxygen saturation ($SpO_2$) monitoring, and skin temperature monitoring, such that the resulting data can include heart rate (HR)/beats per minute (BPM), heart rate variability (HRV), pulse wave slope and relative amplitude, oxygen saturation ($SpO_2$), skin temperature, Respiratory Sinus Arrhythmia (RSA), Low-Frequency Heart Rate Variability (LF-HRV), acceleration in one or more dimensions, etc. Based on the current state of the user, the system can then signal/stimulate the user's nervous system via vibratory and auditory stimuli, where the delivery makes use of machine learning algorithms. The result is a device which improves cognitive and productive states by targeting vagus nerve stimulation and offering hyper-individualized interventions.

The system can include at least two parts: (1) a semi-rigid smart neck band (hereafter referred to as a "neck band") with embedded (e.g., non-invasive, vital sign detecting) sensors, at least one processor, communication systems (e.g., Bluetooth, RF, Zigbee, Wi-Fi, input/output (I/O) ports, etc.), vibratory/auditory emitters, and/or a power source; and (2) control systems which control how the neck band operates. In some configurations, the control systems are integrated into the neck band, with the one or more processors of the neck band analyzing data collected by the physiological sensors and generating vibratory/auditory output via the vibratory/auditory emitters. In such configurations, the user may control the operations of the neck band by pressing buttons, switches, etc. embedded into the neck band, causing the neck band to produce desired outputs accordingly. In other configurations, the control systems are separate from the neck band, such that the user can control the neck band using a smartphone, desktop monitoring system, or other computer system. For example, if the neck band is configured to include Bluetooth or Wi-Fi (Wireless Fidelity) communication systems, the user may be able to control operations of the neck band via an application ("app") on a smartphone. Likewise, if the neck band is configured to receive and/or communicate via cellular and/or RF (Radio Frequency) signals, the neck band may be able to receive instructions via cellular, satellite, or other communication systems. For example, if the user wearing a neck band is operating in a location or situation where management of the neck band by the user themselves is not appropriate or feasible, another user may be able to control the operations of the neck band and relay those instructions to the neck band via cellular or satellite-based signals.

In some configurations, additional devices embedded with sensors, emitters, control systems, communication systems, power systems, etc., can be included in the system. For example, in some configurations, rather than having solely a neck band, the system can include a neck band and a wrist band, where the system collects data from sensors embedded in the neck and wrist bands, makes determinations regarding the user's current state, and generates vibroacoustic output to help bring the user to a desired state. Combining vibratory and auditory stimuli into vibroacoustic output can leverage multiple sensory pathways, which can enhance the efficacy of the stimuli. Synchronizing these stimuli (i.e., both the vibratory and auditory stimuli into the vibroacoustic output) can create a more immersive and effective treatment experience. Non-limiting examples of locations where additional devices may be located include wrists, ankles, ears though other locations are likewise within the scope of this disclosure. In some configurations, rather than a neck band, the device may take the form of a garment, such as a shirt, shorts, shoes, undergarments, etc. Unless otherwise specified, references to a "neck band" herein also apply to other devices, with the exception being that nerve stimulation depends on the location of the additional device being sufficiently close to a desired nerve in the human body.

To perform the physiological monitoring, the neck band can contain embedded sensors which measure one or more of heart rate, heart rate variability (HRV), oxygen saturation ($SpO_2$), activity, pulse wave topography, pulse transit time (PTT), electroencephalogram (EEG), ECG, and/or skin temperature. Non-physiological sensors which can likewise be embedded within the neck band can include an accelerometer or gyroscopes. Additional types of sensors which can be used to understand the user's physiological and/or cognitive states can likewise be embedded in the neck band. These combined measurements provide a neurophysiological foundation for assessing cognitive and emotional states. In some configurations these measurements (i.e., the heart rate, oxygen saturation, skin temperature) can be collected by a common sensor, whereas in other configurations distinct sensors can be used for distinct measurements (e.g., an ECG specific sensor to collect heart rate and HRV data, and a separate $O_2$ sensor for collecting oxygen saturation data).

Collection of the ECG data can include using metal contacts in electrical contact with the ECG sensors embedded in the neck band. The ECG data can then be processed by the control system using a signal processing method resulting in a clean ECG waveform which can be used for accurate HRV analysis. The ECG data collection process and signal processing allows for isolation of a clean ECG wave from data collected at the neck region of a user. First, the electrical signature of the ECG is captured in multiple simultaneous locations around the neck. This is done through a differential amplification scheme that creates all possible pairwise combinations of skin contacts as source signals. The system can use, four example, four signal source contacts on the neck plus an additional contact that is used as a bias reference voltage for all single contact channels. The 4-choose-2 operation yields six sources of the ECG waveform. These six signals are fed to a FastICA (Fast Independent Component Analysis) algorithm in an initial time-slice of five seconds. Please note that this initial time-slice can be as short as 1 second to as long as 2-minutes, but is typically 5-15 seconds. The FastICA algorithm is configured to maximize the kurtotic entropy between extracted components. A rotational transformation is derived through the FastICA algorithm that maximizes the uniqueness of the extracted component based on their kurtotic entropy. A second algorithm inspects the extracted signals and selects the optimal ECG waveform from them for analysis. A periodic process can re-run the FastICA and check for improved ECG extraction and switch to that alternative signal at any point during operation. This periodic process can be triggered by changes in the quality of the extracted ECG, or by the presence of large motion artificacts that can indicate the device has shifted location on the user. All input channels can be pre-processed prior to ICA to mitigate artifacts and/or normalize the energy in each input channel.

While the ECG sensors can be placed throughout the neck band, in particular they can be located over both the left and right upper trapezius muscles. Alternatively, rather than ECG sensors the neck band can contain electromyography (EMG) sensors which measure the health of muscles and the nerves that control them, such as the health/nerve status of the trapezius muscles. While the collective sensors create data with multiple signals, in practice some of these output channels contain specific information on the left/right upper trapezius activity, which can be used to collect information regarding the stress state of the user.

In addition to ECG or $SpO_2$ sensors, the neck band can have embedded optical pulse oximeter sensors. An optical pulse oximeter sensor can be used to measure pulse transit time (PTT) from the ECG R-wave (i.e., the electrical stimulus as it passes through the heart's ventricular walls, visually identified as the largest wave in the ECG representation of a pulse) to the pulse wave arrival. PTT can be corrected to provide a more reliable estimate of blood pressure. In configurations where the neck band contains optical pulse oximeter sensors, the system can measure PTT with using the sensors within the neckband. If desired, a blood pressure measurement or corrected PTT can then be calculated by the system's control systems.

Further extraction of a proxy noninvasive blood pressure signal can provide unique information on the stress and health state of the user. Combining the $SpO_2$ time-series with the optimized ECG results in an accurate pulse transit-time (PTT) signal based on the pulse wave arrival time and the ECG R-wave timing. $SpO_2$ can be measured in the neck region from a surface mounted sensor in the neck band device. PTT can then be measured on a beat-to-beat basis. The measured PTT can then be processed by an algorithm that will remove sources of variance in the beat-to-beat PTT due to rhythmic and aperiodic disruptions determined by movement (i.e., using accelerometer signals and data), heart rate, respiration (derived from the R-wave amplitude time-series), and skin temperature. This modified PTT time-series more closely approximates continuous non-invasive blood pressure. The PTT-Non-Invasive Blood Pressure (NIBP) signal can then be used as an input to the machine learning algorithm that determines when the user requires vibroacoustic stimulation to modulate autonomic state.

Based on the physiological measurements, the control system can then calculate and generate appropriate vibratory and/or auditory stimuli signals for ANS regulation, where those vibratory and/or auditory stimuli cause vagal activation (and preferably optimize) ANS regulation within the context in which the user is monitored. In one configuration the optimization can reduce the intensity of the largest sympathetic arousal events each day. This may lead to increased parasympathetic tone and greater variance in parasympathetic output over the course of each day (i.e., the user will increasingly rely on the parasympathetic branch to navigate responses to arousal events without recruiting sympathetic arousal as frequently). In other configurations the optimization could be different (e.g., keeping a user from falling asleep).

In some configurations, the users (or those monitoring the users) can select between vibratory and/or auditory feedback being generated by the neck band. Such selection can, for example, be made by the user wearing the neck band via a switch or button on the neck band, via an app on the user's smart phone (with instructions regarding that selection then communicated via Bluetooth/RF to the neck band), via a desktop monitoring system (which can then relay the instructions to the neck band via phones, RF, satellite, etc.).

In some configurations, the vibratory/auditory emitters can include bone conduction emitters (BCE), while in other configurations the emitter may include haptic engines controlled by a motor control unit. In some configurations, the emitters are auditory/acoustic only (i.e., speakers), without the haptic/vibratory outputs. In other configurations, the emitters are haptic/vibratory only, without the acoustic outputs. The vibroacoustic output generated by the vibratory/auditory emitters can have a frequency which varies according to a desired condition. Preferably, the vibroacoustic output generated by the vibratory/auditory emitters target the mechanoreceptors of the vascular system. While the range of frequencies at which the vibratory/auditory emitters can generate vibroacoustic output can vary depending on the makes/models of the vibratory/auditory emitters, an exemplary range of frequency at which the vibratory/auditory emitters can generate output is 10-1000 Hz. Preferably, the vibratory/auditory emitters can generate output in at least the 60-100 Hz range.

Preferably, the neck band contains at least two vibratory/auditory emitters which are bilaterally located over the carotid area of the neck. When stimulation occurs, the stimulation can generate the vibroacoustic output either synchronously or asynchronously via the at least two lateralized vibratory/auditory emitters. When the vibroacoustic output is synchronous, each of the at least two vibratory/auditory emitters simultaneously generate the output, which can then be modulated at a defined frequency. For example, a given treatment may have a pulse of vibroacoustic output generated every twenty seconds for two minutes. While the pulses are generated every twenty seconds, each output may only last fifteen seconds (i.e., a five second break between pulses). In this example, in a synchronous configuration, each of the at least two vibratory/auditory emitters will simultaneously generate the fifteen second stimulation followed by a five second rest. When the vibroacoustic output is asynchronous, each vibratory/auditory emitter generates an output which may or may not overlap with the other pulse. Using the same pulse lengths/periods as the example above, if emitter A begins at t=0 s, and emitter B begins at t=10 s (such that each emitter is generating output every twenty seconds, offset from one another by ten seconds), with a fifteen second pulse and five second rest, this means that while emitter A is concluding its pulse emitter B will start, and that while emitter B is concluding its pulse emitter A will start, until the stimulation cycle ends. Vagus nerve stimulation by the vibroacoustic output can, for example, be measured based on changes in heart rate. For example, if the heart rate of the user changes within 5-10 seconds after initiation of the stimulation, this can show that the vibroacoustic output, and the stimulation overall, are having an effect on vagal regulation of the user.

In some configurations, the vibroacoustic output can be modulated at a defined frequency. For example, the vibroacoustic output can be thirty seconds long and modulated at a frequency of 80 Hz. However, in some configurations the modulation can vary. For example, a vibroacoustic output with a center frequency can vary the modulation across the full frequency range (e.g., from 60-100 Hz, or from 40-120 Hz) from low to high or from high to low within the stimulation window. The frequency range can be associated with a particular treatment, and thus be a predefined range, or can vary based on the AI/machine learning algorithm. For example, in some configurations the center frequency can be varied by the machine learning algorithm as the machine learning algorithm searches for a best response to a given treatment.

The stimulation window/cycle can be of any length desired, with periods and/or frequencies which can likewise vary. For example, a stimulation window/cycle may be two minutes, five minutes, ten minutes, or any other duration desired. In practice, the AI/machine learning algorithm can constantly evaluate the state of the user and make refinements to the length/periods/frequencies/frequency ranges of stimulation as needed. In some configurations, if the user would like to specify a specific treatment cycle (e.g., a five-minute relaxation cycle, a 1-minute focus cycle, etc.), the user can make such a selection.

The vibroacoustic output can have a strength or output which varies based on the emitters used, as well as personal preferences. In some configurations, the user can change the volume of the bone conduction emitters (BCE) or haptic engines to meet their personal preferences. Likewise, in some configurations, the user can change the vibrational intensity to meet their preferences. Preferably, the audible effect of the bone conduction by a BCE/haptic engine is in a range of 25-80 dB C-weighted Sound Pressure Level (SPL).

The system (i.e., the neck band+control systems) can also make use of AI/machine learning. In some configurations the AI/machine learning can occur via processing executed on the device (e.g., via a processor embedded into the smart neck band), whereas in other configurations the processing can be executed remotely (e.g., via an application ("app") on a smart phone, on a server, or via a cloud computing system).

The system can use AI/machine learning to continuously monitor the physiological data, improve signal extraction, and personalize interventions. As stated above, computations associated with executing AI/machine learning algorithms can occur via the processor(s) embedded within the neck band, on a wireless connected smartphone, on a desktop computer or other computing device (e.g., a tablet, a server, etc.), or via a cloud computing system. The AI/machine learning algorithms analyze the physiological data and extract from that physiological data the user's current state and provides appropriate interventions. In some instances, this process can be automatic, where the system can detect based on the user's location, the user's movement, the time of day, etc., a desired condition for the user. Then, based on the detected state of the user based on the collected physiological data, the AI/machine learning algorithm can identify a pattern of vibratory and/or auditory stimuli recruiting vagal activation which will bring the user from the user's current state to the desired condition. For example, if the user is currently in an active state but needs to be in a relaxed (e.g., sleep) state, the AI/machine learning algorithm can generate a pattern to bring the user to the relaxed state. In other instances, the user can manually specify a desired condition (e.g., recovery, sleep, performance, rest and restore, relax and unwind, etc.). As with the automatic process, the system can then, based on the detected state of the user based on the collected physiological data, identify a pattern of vibratory and/or auditory stimuli recruiting vagal activation which will bring the user from the user's current state to the desired condition.

The system can, for example, use AI to analyze the incoming data (e.g., the physiological data plus any additional sensors, such as movement data from the accelerometer) to determine a current state of the user. Such AI systems can be, for example, a neural network. The neural network can be trained using historical data of previous users with known states (e.g., relaxed, agitated, focused, etc.). Once the neural network is trained, it can be converted to code which can be executed as an algorithm by one or more processors. Inputs to the algorithm can include the current sensor data, while output of the algorithm can be a current state of the user.

The system's machine learning can be used, with or without AI, to personalize stimulation parameters in order to maximize the efficacy of the stimulation. The machine learning uses (1) an "outside" feedback loop which is constantly tracking changes in physiological condition and triggering stimulus when subject meets the conditions for a stimulation, and (2) an "inside" feedback loop which is only active while a stimulus is turned on. For example, the system can detect (using the outside feedback loop) when the user is experiencing stress, then initiate a stimulus (also initiating the inside feedback loop) in response.

The outside feedback loop can, in some configurations, be the AI system described above, with inputs to the outside feedback loop receiving the sensor data (e.g., heart rate, HRV (including both Respiratory Sinus Arrhythmia (RSA) (aka high-frequency HRV) and low-frequency HRV, oxygen saturation, activity level per accelerometer, PTT, etc.). This data can be collected periodically (e.g., every five seconds), and outside feedback loop of the machine learning algorithm can calculate the user's state based on those inputs. Once the conditions (e.g., the user's state, plus time of day, activity level, manual instructions, etc.) indicate that a stimulus should be triggered, the outside loop triggers the stimulation, and an inside/second feedback loop initiates.

The inside loop of the machine learning looks at the growing history of times this user was stimulated, and the machine learning adjusts the parameters of the stimulation to try to find parameters that work well for this particular person. Thus, the inside loop not only considers if the overall changes in the user state reflect the desired goal (i.e., is the user state changing as desired), but also the rate of change in the user's state. Inputs to this inside loop can include the change in heart rate during the current stimulation, the change in HRV (RSA and/or low-frequency HRV), etc. Based on the efficacy of these changes, the inside loop can change how the stimulation occurs. For example, the inside loop may determine that last week when an identical stimulation was made, the user responded better with a twenty-five-second-long pulse, compared to a twenty-second-long pulse. When trying the same stimulation again (meaning, trying to obtain a same desired state from a same starting state of the user), the inner loop may test the parameters of the stimulation while it is being executed to determine an even better pulse length. For example, the inner loop may change the duration from twenty-three seconds to twenty-eight seconds, recording the user's change in heart rate, HRV, etc., and determining the patterns which work the best for the user. Other non-limiting ways in which the inner loop can vary the stimulation can include stimulus intensity (e.g., the volume or pressure being applied by the emitters), the stimulus frequency, the stimulus length, the center frequency, the frequency sweep (how fast the frequencies within a range are modulated during a stimulation), the duty cycle of the stimulation (i.e., the duration of one amplitude modulation phase), the interval between stimulation pulses (i.e., the gap), etc. Over time, the patterns can become more refined, and more user-specific, thus improving the system's ability to affect the user's state in a desired manner.

In some configurations, the machine learning can also make determinations on how to better configure the stimulation parameters between stimulation sessions. For example, the system, upon review of the data, may determine that a central frequency shift might assist the user with regard to a given stimulation. In this example, the system may be generally operating under a 'search' algorithm looking for the right frequency for this user within a frequency range (e.g., 10-100 Hz). Once a stimulation session starts, the system may set a small range/portion of that overall frequency range that the system can modulate within this session (e.g., 80-90 Hz). Then, on a shorter (e.g., one second) cycle the system can search within this 10 Hz smaller range. In this manner, the system sets a general target, then continues to use smaller, faster, more precise searches to try to maximize response during the session. In this manner the inner loop described above can help the system search and find the forms of stimulation which best help a given user. The system can also integrate with other health monitoring systems and electronic health records (EHRs) to provide a more comprehensive health management solution, thereby updating stimulation parameters using data beyond the sensor data collected from the neck band.

The machine learning can also update weight given to a given sensor on the neck band. For example, over time as the system learns which sensors (or sensor types) provide the best information to make an accurate prediction regarding the user state, the system can weigh those sensors and/or sensor types more when making predictions. These individual components of the overall sensor data can be continuously monitored and updated based on the observed quality of the ECG signal(s) and/or EMG signal(s). The system can replace the current weights associated with individual components with new weights if the observed quality of a new set of weights exceeds the current weights. This process of updating the weights used by the machine learning algorithm to predict user state can be a feedback loop running at the level of the sensor data extraction and can be independent of other algorithms executed by the control system.

The machine learning (and, in some configuration, use of AI) allows for continuous monitoring, individualized interventions, real-time analysis, and feedback, thereby ensuring that the system adapts to the user's physiological changes dynamically. In some configurations, the machine learning can not only react to current states of the user, but also predict future states based on historical data and trends, thereby offering preemptive interventions. For example, if the user consistently generates ECG data indicating stress at a specific time of day, the system can recommend to the user (via an app or other user interface), before that specific time of day, to undergo a relaxation stimulation, thereby trying to preemptively intervene in the stress.

In some configurations, the system can communicate the best practices for a given user back to a central database, where they can be compared against other users. Based on averages of multiple users, the system can program future stimulations for new users which, based on previous "group-sourced" data, has a higher likelihood of successfully achieving the desired outcomes. In such circumstances, the system can take into account demographic data of the user such as age, sex, weight, health status, job, etc., and, where applicable, use that demographic data to identify individuals with similar backgrounds, the idea being that individuals of similar backgrounds may respond similarly to stimulations.

The cognitive and emotional states of the user can be predicted through the sensor data, specifically the heart rate (HR) and HRV data. After controlling for predictable impacts on HR/HRV from time of day and metabolic demand (due to physical activity and posture), the system can track changes in the relative levels of HR/HRV parameters and optimize for greater HRV and lower HR for each user. In some circumstances the system may use additional sensor data (e.g., the blood oxygenation level, accelerometer data, etc.) to determine the user's state. Based on the detected state of the user, the system can then seek to enhance the neural regulation of the user's autonomic nervous system. More specifically, at the device level, the system can generate stimulations which: lower heart rate at a given time of day; increase HRV at a given time of day; create a greater range of heart rate across the day; and/or create a greater range of HRV levels across the day. Likewise, the system can generate stimulations which can cause changes in the user's other physiological states (e.g., increasing HR, improving oxygenation, etc.). For the user's overall wellbeing, the system can improve the brain's ability to control and coordinate the activity of the Autonomic Nervous System (ANS). The ANS is responsible for regulating involuntary bodily functions, such as heart rate, digestion, respiratory rate, and blood pressure, through two main branches: the sympathetic (responsible for fight-or-flight responses) and the parasympathetic (responsible for rest-and-digest functions). The system can also enhance neural regulation, which can include:

(A) Optimizing Balance Between Sympathetic and Parasympathetic Activity: This involves improving the coordination between activating (sympathetic) and calming (parasympathetic) responses so the body can quickly adjust to different demands, whether they are stress-related or restorative.

(B) Improving Flexibility: A well-regulated system is flexible and capable of efficiently shifting between different states of arousal and relaxation. For example, it can engage in social interactions (which are associated with parasympathetic activity) or mobilize energy for challenges (sympathetic activation) when needed, without becoming stuck in either state.

(C) Supporting Resilience: Enhanced neural regulation strengthens the capacity to return to a calm, restorative state after experiencing stress, reducing the likelihood of chronic stress or autonomic dysregulation.

(D) Fostering Social Engagement: According to Polyvagal Theory, better neural regulation of the ANS supports prosocial behavior and emotional regulation. When the ventral vagal complex (part of the parasympathetic nervous system) is properly engaged, individuals are better able to feel safe, connected, and socially engaged.

Based on these principles, the system disclosed herein can assist users in regulating their ANS, their emotional states, their parasympathetic nervous system, and their cognition. A non-limiting example of calming the parasympathetic nervous system can include providing stimulation(s) which increase HRV, decrease HR, and slow the breathing rate (which can be estimated from the frequency feature of the user's RSA). Likewise, a non-limiting example of calming which results in enhanced performance can include a faster, more efficient response of the parasympathetic system. Cognitive/emotional improvements may vary significantly on individual users, however non-limiting examples of such improvements can include improved affect, focus, sleep quality, and reduced anxiety and depression symptoms.

In some configurations, the system may collect data for later analysis by the control systems, the user, and/or other with access to the user's data. For example, the system can detect when the user is experiencing stress (or other emotions), then provide that information to the user in a dashboard (e.g., via an app), allowing the user to see that they have a strong stress response at a predictable point in the work-day every week. Similarly, if a group/team of individuals wearing neck bands is sending data back to a central hub for review by a supervisor, the system can analyze the data of everyone on the team and provide a report to the supervisor of when the team collectively experiences stress. In this manner, individuals (or teams) can review their emotional/cognitive patterns based on the data collected by the neck bands and analyzed by the system's control systems. Alternatively, the data of individuals may be provided to a healthcare provider, allowing the healthcare provider to track patients' physiological data and intervene when necessary.

In some instances, users may not want to wear the neck band all day, but rather use the neck band as a sleep tool. In such cases, the system operates in the same manner as otherwise described herein, with an emphasis on relaxation. As otherwise described herein, the system can work to optimize and enhance the user in their task—sleeping. To do so, the system can collect physiological and movement data while the user is sleeping or preparing to sleep and can provide stimulation to relax the user and/or otherwise assist the user in obtaining their desired rest.

In high-stress occupations, the system can be used to monitor workers' stress levels and provide interventions to prevent burnout and improve productivity. These results can be provided individually to the users (i.e., the workers) wearing the neck band, or can be provided to a supervisor or manager who can evaluate the overall well-being of the workers. For example, the system can be part of corporate wellness programs, offering employees a tool to manage stress and improve overall well-being, and/or providing group goals. Beyond stress and anxiety management, the system disclosed herein can be used to enhance cognitive functions in various settings, such as for students during study sessions or professionals during high-stress work periods. The system can also support mental health treatment plans by providing non-pharmacological interventions for conditions like depression, anxiety disorders, and Post Traumatic Stress Disorder (PTSD). In addition, by monitoring physiological metrics and providing real-time feedback, the system can be used to assist in fitness training and recovery, ensuring that users stay within optimal ranges for heart rate and HRV during exercise. Likewise, for users in physical rehabilitation, the system can be used to monitor and enhance recovery by ensuring the ANS is optimally regulated, thereby improving outcomes for patients recovering from surgeries or injuries. For patients with chronic diseases such as cardiovascular diseases, diabetes, and chronic pain, the system can be used to help manage symptoms by continuously regulating the ANS and providing timely interventions to mitigate adverse physiological responses. For the Department of Defense (DoD), the system can be used to enhance soldiers' readiness and resilience by managing stress and optimizing cognitive function in high-pressure situations, in addition to providing aid in the recovery and rehabilitation of veterans suffering from PTSD and other stress-related conditions.

The system disclosed herein can operate in both closed-loop and open loop configurations. In a closed-loop configuration, the system can provide automated, real-time adjustments to the user's physiological state, enhancing the device's effectiveness in managing stress and anxiety. In an open-loop configuration, the system can allow for user input and manual adjustments, giving users control over their treatment and potentially increasing user engagement and adherence. In some configurations, the system operates as a combination of open-loop and closed-loop. For example, the system may be generally configured to operate automatically in the closed-loop configuration but allow for the user to override the automatic settings to follow a specific, manually selected program.

FIG. 1 illustrates an example system with a user 102 wearing a wearable device 104 in wireless communication with a mobile communication device 106. As illustrated, the wearable device 104 (e.g., a neck band) detects the user's 102 heart rate variability (HRV) (1) 108. While not explicitly illustrated, the wearable device 104 will generally have a variety of sensors embedded therein, such as ECG sensors, EMG sensors, accelerometers, etc. Preferably, at least some of these sensors make contact with the skin of the user 102, allowing capture of data such as HRV. The wearable device 104 then transmits the HRV (2) 110 to a computing device 106, such as a smartphone, tablet, or other computing system. The computing device 106 identifies a current state (3) 112 of the user 102. The computing device 106 then identifies a desired state (4) 114 of the user 102. The desired state can be determined automatically via the computing device 106 or can be manually entered by the user 102 into the computing device via a user interface. Once the desired state is identified (4) 114, the computing device identifies a treatment for the desired state (5) 116. In other words, the computing device identifies a treatment, or planned stimulation, for bringing the user 102 from the current state to the desired state. As discussed herein, this treatment can involve the wearable device 104 generating vibration and/or acoustic output which affects the user's 102 autonomic nervous system. Having identified the treatment (5) 116, the computing device 106 transmits the treatment (6) 118 to the wearable device 104, at which point the treatment (7) 120 is executed by the wearable device 104. This process can continue indefinitely.

Figure 2:
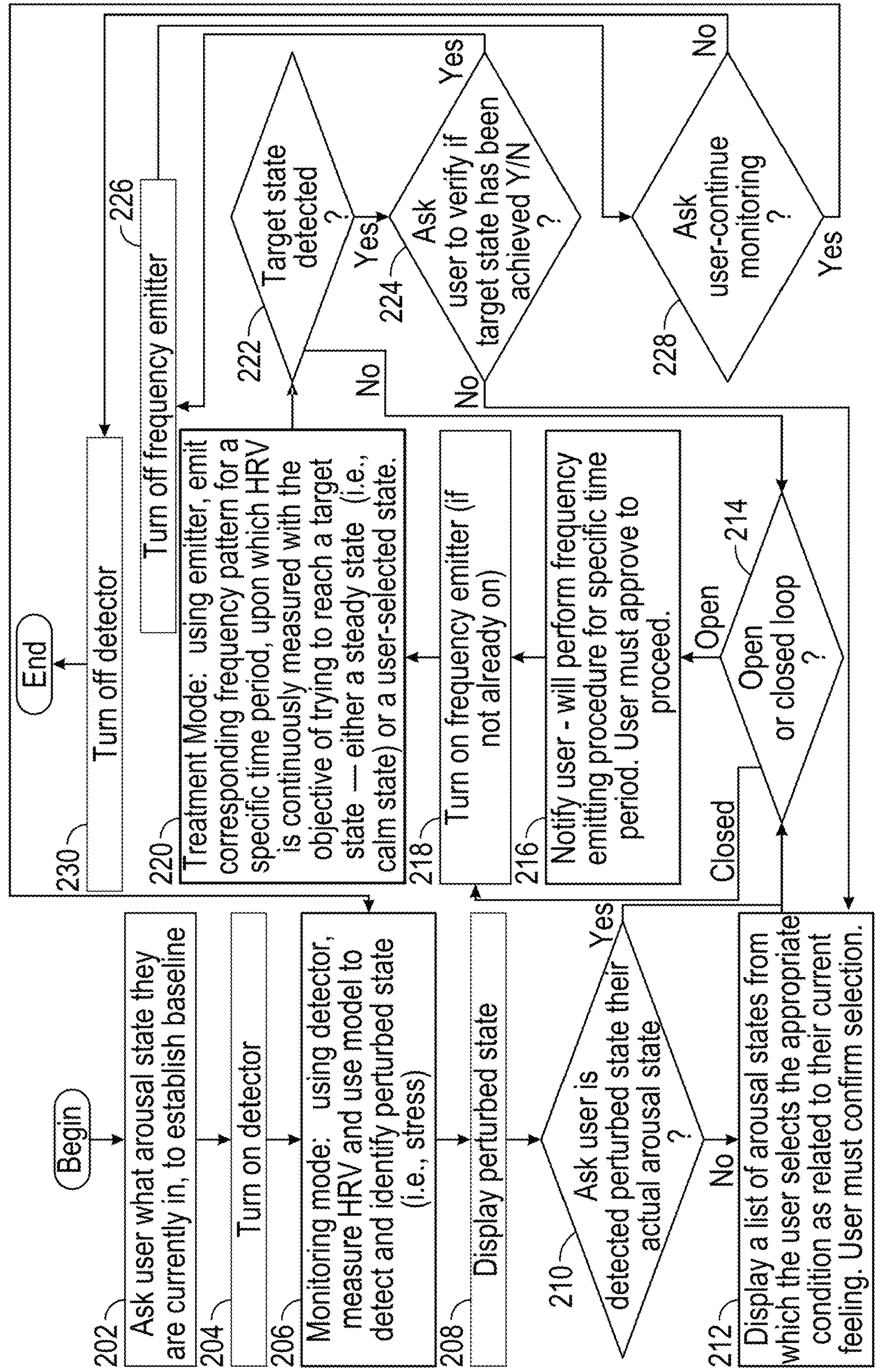
FIG. 2 illustrates an example method for regulating the Autonomic Nervous System (ANS) via a wearable device.

FIG. 2 illustrates an example method for regulating the Autonomic Nervous System (ANS) via a wearable device. In this example, the system asks the user what arousal state they are currently in, to establish a baseline (202). The system then turns on a detector (204) (i.e., the system turns on the sensors embedded in the neck band) and using the detector the system can enter a monitoring mode (206). The monitoring mode (206), using the detector, allows the system to measure Heart Rate Variability (HRV) and use trained models to detect and identify if the user is in a perturbed state (i.e., stress). In other instances, other states of the user can likewise be identified. The system then displays a notification of the perturbed state (208) to the user (e.g., via a user interface; preferably this user interface is on the user's smartphone or computing device) and asks the user if the detected perturbed state is their actual arousal state (210). If the user indicates "No", that they are not actually perturbed, the system can display a list of arousal states from which the user can select the appropriate condition as related to their current feeling, with a confirmation of the user regarding the selection (212).

Regardless of whether the initial determination of a perturbed state is correct, or if the user makes a selection (212) of their state, the system next determines if it is in an open or closed loop configuration (214). In an open configuration, the user will be notified that the system is going to perform a frequency emitting procedure for a specific time period, and the user must approve of this to proceed (216). At this point the system can turn on a frequency emitter (if not already turned on) in the user's wearable device (218). If in a closed configuration, the system can automatically turn on the frequency emitter (218), without the user's additional permission. The system will then enter a treatment mode (220), where, using the frequency emitter, the system emits a corresponding frequency pattern for a specific time period, during which the HRV (or other physiological data) of the user is continuously measured. The goal is for the user to reach a target state, such as a steady state (i.e., a calm state) or a user-selected state.

The system continuously checks to see if the target state is detected (222). If not, the system will restart the treatment cycle, beginning with the verification of open/closed loop (214). If the target state has been detected, the system can ask the user to verify if the target state has been achieved (224). If not, the process can again begin the process anew, reverting to the display of possible arousal states for the user to select from (212). If the user indicates that the target state has been reached, the system can turn off the frequency emitter (226), then ask the user if it should continue monitoring (228). If no, the system can turn off the detector (230). If the user indicates that the system should continue monitoring, the process can begin again with the monitoring mode (206).

Figure 3A:
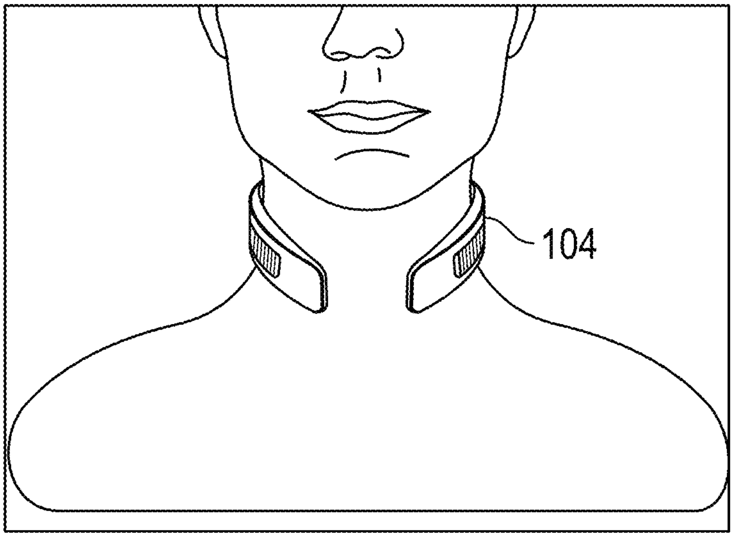
FIG. 3A illustrates a user wearing a neck band.

FIG. 3A illustrates a user wearing a wearable device 104 (i.e., a neck band). As illustrated, the wearable device 104 preferably fits around the neck, and specifically fitting bilaterally over the carotid area of the neck. In other configurations, the wearable device 104 can be configured to extend further than the illustrated example, with the wearable device 104 extending to the trapezius muscles, the ears, or other parts of the neck.

Figure 3B:
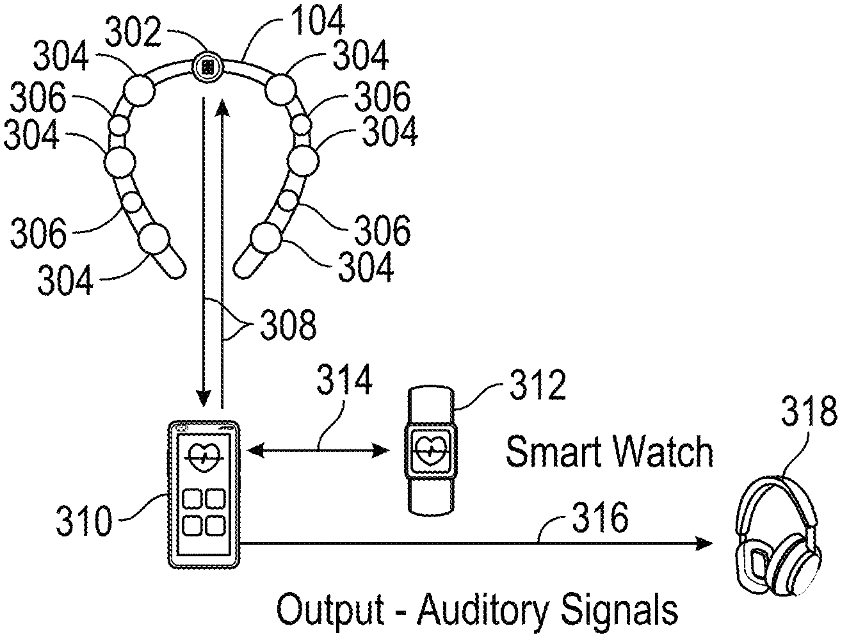
FIG. 3B illustrates an example of the wearable device interacting with a smartphone and other devices.

FIG. 3B illustrates an example of the wearable device interacting with a smartphone and other devices. As illustrated, the wearable device 104 has at least one control center 302 built into it, along with emitters 304 and sensors 306. Note that the number of emitters 304 and sensors 306 is purely exemplary and may vary as needed. The control center 302 contains one or more processors which collect data from the sensors 306, and which can provide instructions to the emitters 304. The control center 302 can also enable communications 308 (e.g., via a Bluetooth transceiver, a wireless communications port, etc.) to/from a computing device, such as a smart phone 310. The smart phone 310 can perform analysis on the data collected by the sensors 306, provide instructions regarding treatment/stimulation being provided by the emitters 304, allow the user wearing the wearable device 104 to update settings (e.g., change between manual and automatic stimulation (closed loop/open loop), update desired state, etc. The smart phone can also communicate 314, 316 with auxiliary devices, such as (but not limited to) a smart watch 312, or headphones 318. Devices such as smart watches 312 can collect additional measurements which can be used to determine the user's current state, and if treatment/stimulation has resulted in the user reaching a target/desired state. Devices such as headphone 318 can be used to provide additional output to the user as part of any treatment/stimulation. For example, the smart phone 310 can cause synchronized auditory output via the headphones 318 and vibratory output via the emitters 304. Note that in some configurations the emitters 304 can themselves be capable of auditory output, and the headphones 318 may be unnecessary. In yet additional configurations, some emitters 304 may be vibrational, some may be auditory, and some may be both vibrational and auditory.

Figure 4:
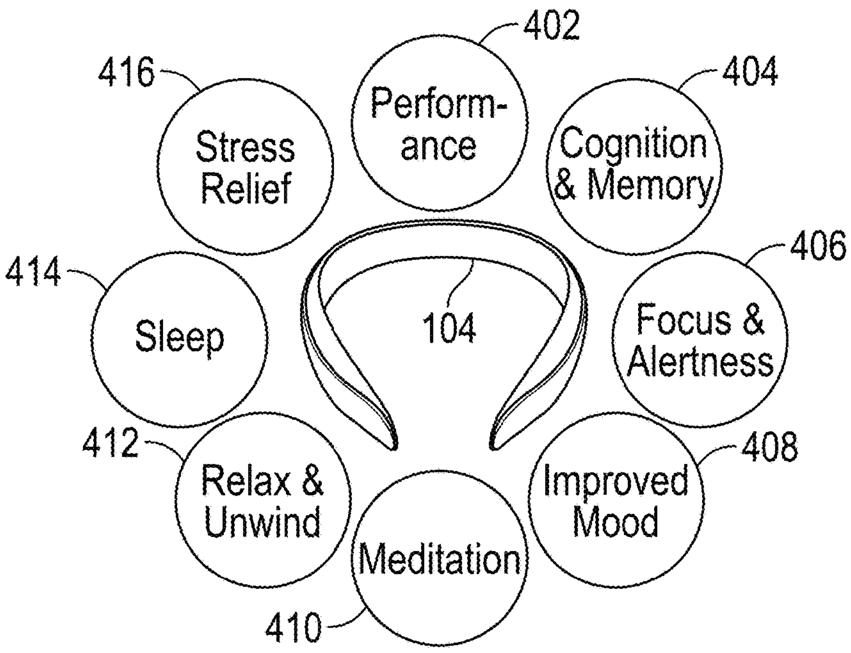
FIG. 4 illustrates an example of targeted benefits of using the wearable device.

FIG. 4 illustrates an example of targeted benefits of using the wearable device 104. Such benefits are exemplary only, and may include: performance 402, cognition and memory 404, focus and alertness 406, improved mood 408, meditation 410, relax and unwind 412, sleep 414, and stress relief 416.

Figure 5:
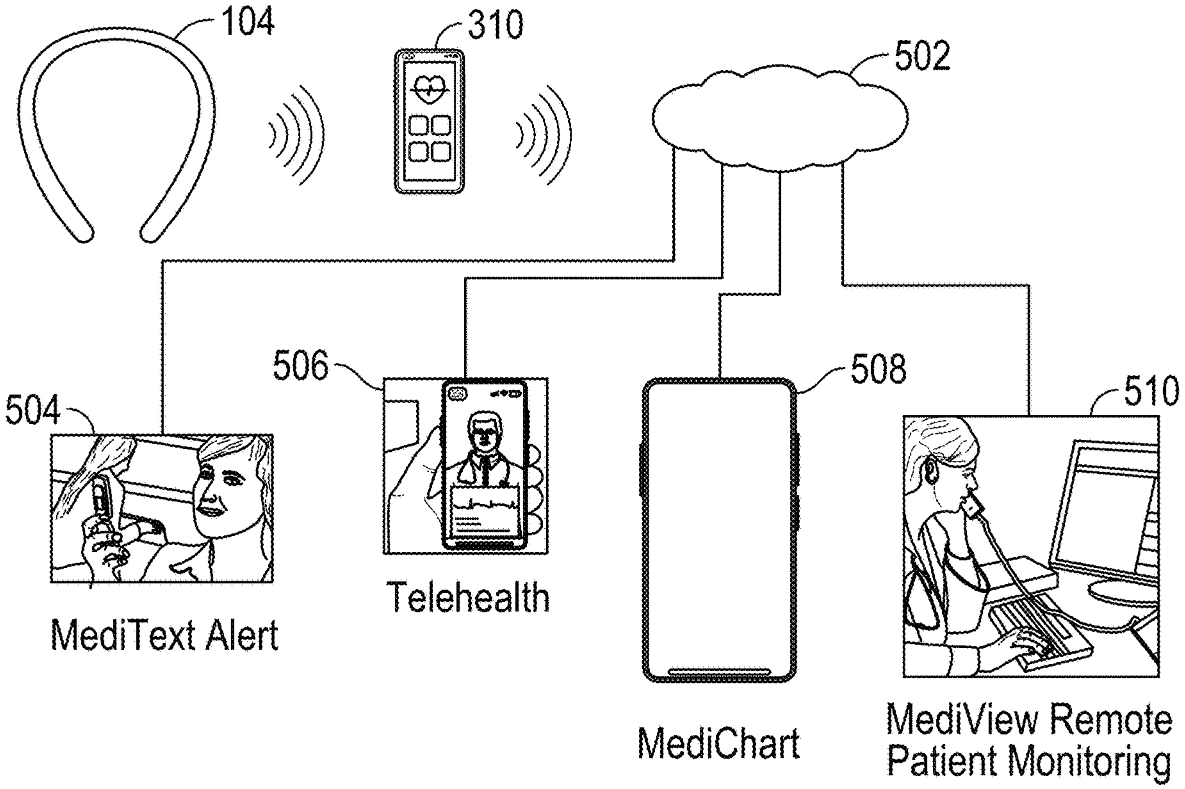
FIG. 5 illustrates an example of a connected care platform interacting with a wearable device.

FIG. 5 illustrates an example of a connected care platform interacting with a wearable device 104. In this example, the wearable device 104 wireless communicates with a smart phone 310, which in turn communicates with a network 502, such as the Internet. Through the Internet conditions associated with the user of the wearable device 104 can be communicated, such that a remote system can analyze the sensor data. Non-limiting examples of the outcomes of this analysis can include a MediText alert 504 to the user (or to emergency personnel) based on the user's status, telehealth 506 initiation based on a status of the user, an updating of the user's medical chart 508 ("medichart"), and/or remote patient monitoring 510 ("mediview").

Figure 6:
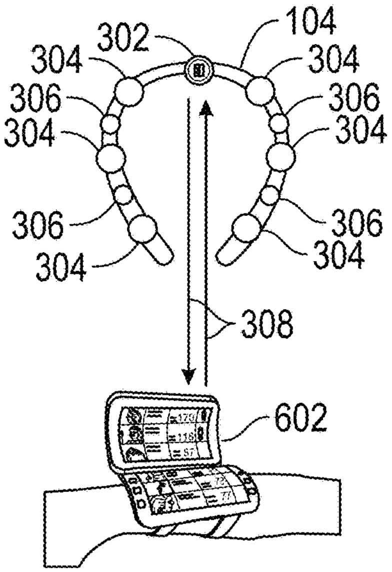
FIG. 6 illustrates an example of the wearable device being controlled via a wrist monitor.

FIG. 6 illustrates an example of the wearable device 104 being controlled via a wrist monitor/communicator 602. As illustrated, rather than communicating with the wearable device 104 via a smart phone 310 as illustrated in FIG. 3B, in this case the system utilizes a wrist-based wearable computer/communication system which functions as (a) a remote central monitor capable of displaying data from one or many wearable devices, (b) a wireless bi-directional two-way voice/video communicator facilitating a medic with the capability of remotely talking and seeing the user and healthcare professionals in a remote location (e.g., a field triage hospital), and/or (c) a GPS (Global Positioning System) device identifying each user location as each neck band can incorporate a GPS. In some configurations, the wrist monitor/communicator 602 can collect additional sensor data and/or provide additional vibroacoustic output which can be synchronized with output generated by the emitters 304 of the wearable device 104. For example, the wrist monitor/communicator 602 can be monitoring vital sign data of the user or multiple users in a manner similar to a central monitoring system typically found in hospital Intensive Care Unit (ICU) central monitoring systems, the wrist monitor/communicator 602 can be used for voice/video communications (a) between the wearer of the neck band and the medic, and/or (b) between the medic and healthcare professionals located in a remote location (e.g., a field triage hospital). The wrist monitor/communicator 602 can be used, for example, (a) during on-site point of injury remote monitoring, (b) within medical triage settings as a wearable central vital signs monitor, and/or (c) during transport (e.g., ground base emergency service vehicle or air-transport). The wrist monitoring/communicator 602 can incorporate the one or more of the following features:

- Folding dual display touch screens for enhanced remote monitoring/multi-tasking capabilities, and internet access;
- Dual mounted high-definition video cameras for patient image recording, two-way voice video conferencing, photographing images;
- A microphone for voice communication and verbal patient annotation recording;
- A built-in digital recorder for recording patient assessment, and for verbal recording of patient medical history in native voice;
- A positioning device (e.g., GPS) for providing real-time location tracking of patients, and other wrist monitor/communicator devices 602;
- Multiple radios (e.g., Global System for Mobile Communications (GSM)/Code Division Multiple Access (CDMA), ZigBee, Wi-Fi) for two-way voice/video communications and Voice over Internet Protocol (VoIP) with the user and other healthcare professionals;
- Built-in flexible solar panels located on top of a flip up display for charging an internal battery;
- Dual hot swapable batteries ensuring continuous battery operation;
- A barcode/Radio Frequency Identification (RFID) scanner for reading medication bottles, military identification tags; and/or
- Ingress Protrextion (IPX) rating for water resistance (i.e., the wrist monitoring/communicator 602 can be water resistant).

Figure 7:
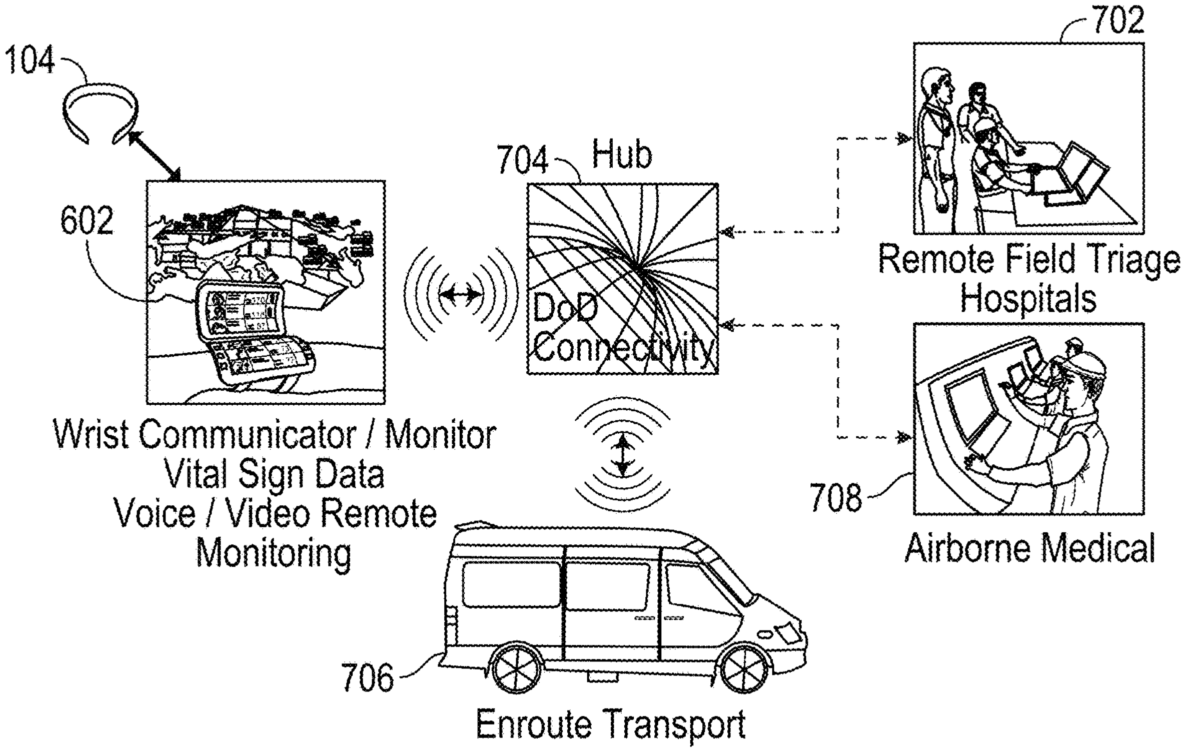
FIG. 7 illustrates an example of the wearable device being used in a military application.

FIG. 7 illustrates an example of the wearable device 104 being used for remote vital sign monitoring of injured people's vital signs in a civilian or military application. In this example, the wearable device 104 is communicating via a wrist monitor/communicator 602. That wrist monitor/communicator 602 then communicates directly with a DoD Hub 704, which can send data about the wearer of the wearable device 104 to others. While in some circumstances that may be a soldier's leadership, in other instances (such as that illustrated), the data can be sent to medical units which can assist the medic in the treatment of the soldier. For example, upon detecting sensor measurements indicating the soldier has been wounded, the DoD Hub 704 can initiate communications with a remote field triage hospital 702, with airborne medical 708, and/or with enroute transport 706, as needed. In other configurations, rather than needing to communicate with the wrist monitor/communicator 602 or a smartphone, the wearable device 104 can have cellular, RF, or other communication capabilities integrated into the wearable device 104, such that the wearable device 104 can communicate directly with the DoD Hub 704 (or other communication systems, such as a satellite, cellular tower, radio relay, etc.). In other configurations the neck band can incorporate GPS communication thereby facilitating the wrist monitor/communicator 602 with the capability of identifying the locations of all the users in relationship to the wrist monitor/communicator 602, an audible speaker facilitating the soldier to hear any communication from the medic, and a microphone facilitating the soldier with the capability of talking with the medic.

The neck band can operate in a wireless mesh configuration via Wi-Fi or Zigbee whereby each neck band acts as a wireless repeater thereby facilitating an expanded wireless network. For example, the neck bands can form a wireless mesh, repeating data/signals between the neck bands until a wrist monitor/communicator 602 (or one of the neck bands) can establish contact with another communication system (e.g., a cellular tower, a satellite, a network platform, etc.).

Figure 8:
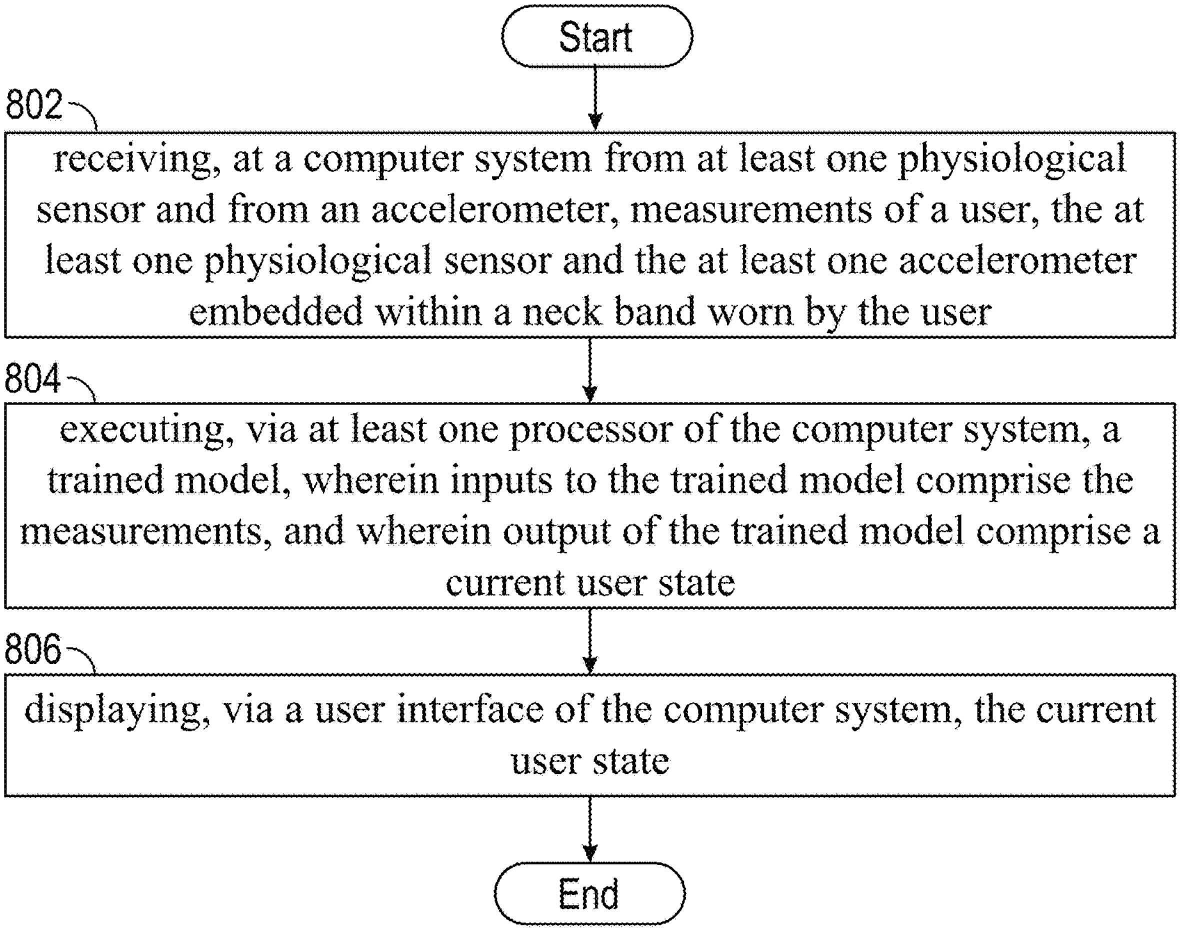
FIG. 8 illustrates an exemplary method embodiment.

FIG. 8 illustrates an exemplary method embodiment. As illustrated, the method can include receiving, at a computer system from at least one physiological sensor and from an accelerometer, measurements of a user, the at least one physiological sensor and the at least one accelerometer embedded within a neck band worn by the user (802). Next, the method includes executing, via at least one processor of the computer system, a trained model, wherein inputs to the trained model comprise the measurements, and wherein output of the trained model comprise a current user state (804) and displaying, via a user interface of the computer system, the current user state (806).

In some configurations, the illustrated method can further include: comparing, via the at least one processor, the measurements against historical data of the user, resulting in a comparison; identifying, via the at least one processor, a vibroacoustic stimulation pattern appropriate for the user based on the comparison; and transmitting, from the computer system to the neck band, instructions to begin the vibroacoustic stimulation.

In some configurations, the illustrated method can further include: comparing, via the at least one processor, the measurements against historical data of the user, resulting in a comparison; identifying, via the at least one processor, a vibroacoustic stimulation pattern appropriate for the user based on the comparison; proposing the vibroacoustic stimulation pattern to the user via a user interface of the computer system; receiving, via the user interface, authorization from the user to begin the vibroacoustic stimulation pattern; and after receiving the authorization, transmitting, from the computer system to the neck band, instructions to begin the vibroacoustic stimulation.

In some configurations, the illustrated method can further include: receiving, from the user via a user interface of the computing system, a user-desired state; generating, via the at least one processor, a stimulation plan to bring the user from the current user state to the user-desired state; and transmitting, from the computing system to the neck band, instructions to begin generating vibroacoustic stimulation according to the stimulation plan.

In some configurations, the computing system can be one of a smart phone or a tablet computer.

In some configurations, the neck band and the computing system communicate wirelessly.

In some configurations, the illustrated method can further include: transmitting, from the computing system to the neck band, instructions to begin generating vibroacoustic stimulation based on the current user state. In such configurations, the current user state can be associated with stress, and the vibroacoustic stimulation can be selected to reduce the stress.

In some configurations, the vibroacoustic stimulation can be generated by emitters located in the neck band, where at least one emitter is within a predefined distance of sensory pathways communicating with a nucleus of the solitary tract and the ventral vagal complex of the person. For example, the predefined distance may be within 5-10 mm of either side (or directly above) the barosensory receptors, as the vibratory stimulation will propagate beyond the point of contact. In another instance, the predefined distance may be 15 mm of the barosensory receptors.

Figure 9:
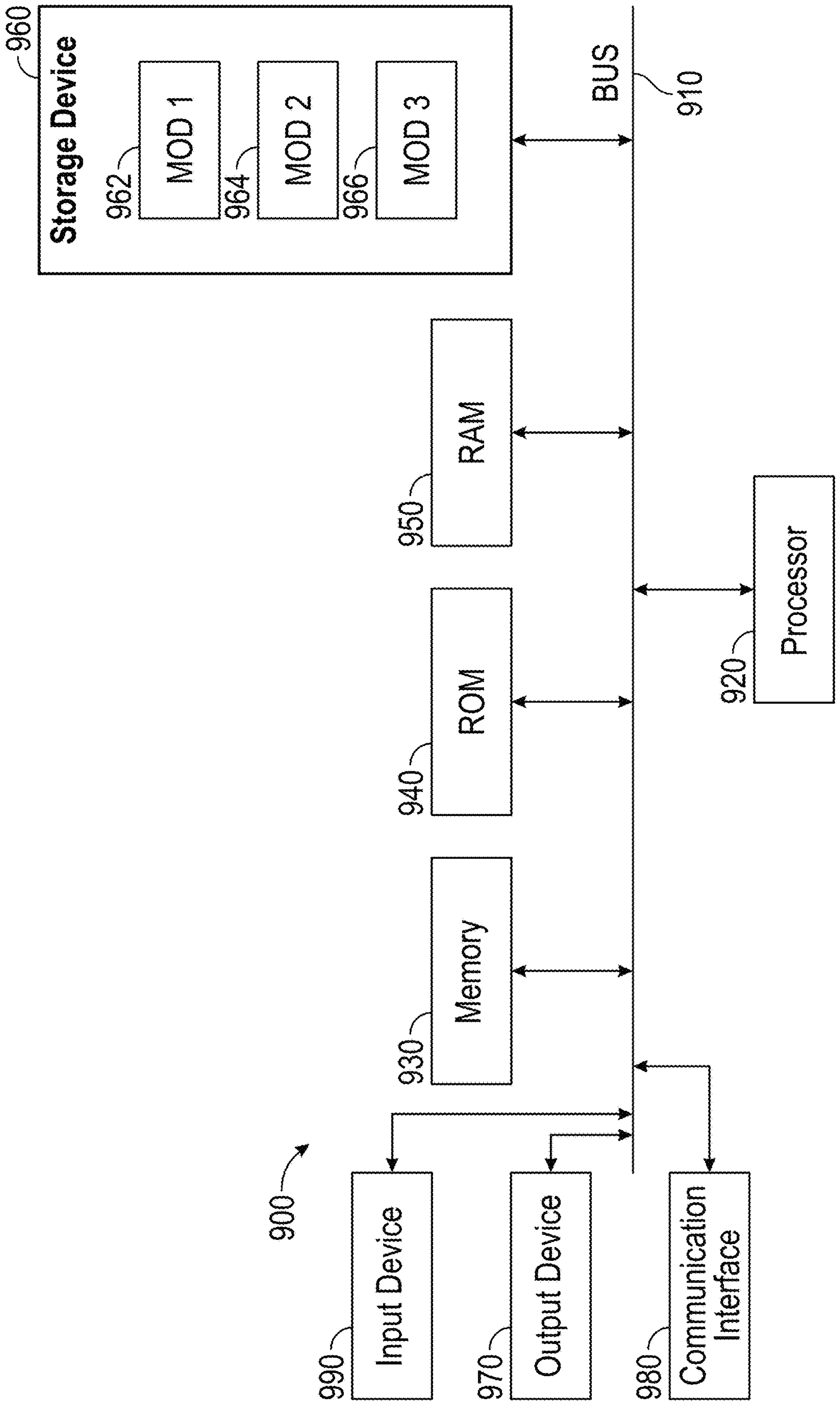
FIG. 9 illustrates an exemplary computer system.

With reference to FIG. 9, an exemplary system includes a computing device 900 (such as a general-purpose computing device), including a processing unit (CPU or processor) 920 and a system bus 910 that couples various system components including the system memory 930 such as read-only memory (ROM) 940 and random access memory (RAM) 950 to the processor 920. The computing device 900 can include a cache of high-speed memory connected directly with, in close proximity to, or integrated as part of the processor 920. The computing device 900 copies data from the system memory 930 and/or the storage device 960 to the cache for quick access by the processor 920. In this way, the cache provides a performance boost that avoids processor 920 delays while waiting for data. These and other modules can control or be configured to control the processor 920 to perform various actions. Other system memory 930 may be available for use as well. The system memory 930 can include multiple different types of memory with different performance characteristics. It can be appreciated that the disclosure may operate on a computing device 900 with more than one processor 920 or on a group or cluster of computing devices networked together to provide greater processing capability. The processor 920 can include any general-purpose processor and a hardware module or software module, such as module 1 962, module 2 964, and module 3 966 stored in storage device 960, configured to control the processor 920 as well as a special-purpose processor where software instructions are incorporated into the actual processor design. The processor 920 may essentially be a completely self-contained computing system, containing multiple cores or processors, a bus, memory controller, cache, etc. A multi-core processor may be symmetric or asymmetric.

The system bus 910 may be any of several types of bus structures including a memory bus or memory controller, a peripheral bus, and a local bus using any of a variety of bus architectures. A basic input/output (BIOS) stored in memory ROM 940 or the like, may provide the basic routine that helps to transfer information between elements within the computing device 900, such as during start-up. The computing device 900 further includes storage devices 960 such as a hard disk drive, a magnetic disk drive, an optical disk drive, tape drive or the like. The storage device 960 can include software modules 962, 964, 966 for controlling the processor 920. Other hardware or software modules are contemplated. The storage device 960 is connected to the system bus 910 by a drive interface. The drives and the associated computer-readable storage media provide non-volatile storage of computer-readable instructions, data structures, program modules and other data for the computing device 900. In one aspect, a hardware module that performs a particular function includes the software component stored in a tangible computer-readable storage medium in connection with the necessary hardware components, such as the processor 920, system bus 910, output device 970 (such as a display or speaker), and so forth, to carry out the function. In another aspect, the system can use a processor and computer-readable storage medium to store instructions which, when executed by a processor (e.g., one or more processors), cause the processor to perform a method or other specific actions. The basic components and appropriate variations are contemplated depending on the type of device, such as whether the computing device 900 is a small, handheld computing device, a desktop computer, or a computer server.

Although the exemplary embodiment described herein employs the storage device 960 (such as a hard disk), other types of computer-readable media which can store data that are accessible by a computer, such as magnetic cassettes, flash memory cards, digital versatile disks, cartridges, random access memories (RAMs) 950, and read-only memory (ROM) 940, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 900, an input device 990 represents any number of input mechanisms, such as a microphone for speech, a touch-sensitive screen for gesture or graphical input, keyboard, mouse, motion input, speech and so forth. An output device 970 can also be one or more of a number of output mechanisms known to those of skill in the art. In some instances, multimodal systems enable a user to provide multiple types of input to communicate with the computing device 900. The communications interface 980 generally governs and manages the user input and system output. There is no restriction on operating on any particular hardware arrangement and therefore the basic features here may easily be substituted for improved hardware or firmware arrangements as they are developed.

The computing device 900 may be described in the general context of computer system-executable instructions, such as program modules, being executed by a computer system. Generally, program modules may include routines, programs, objects, components, logic, data structures, and so on that perform particular tasks or implement particular abstract data types. In configurations where the computing device 900 is used in a distributed cloud computing environment (such as where the computing device 900 utilizes one or more servers) where tasks are performed by remote processing devices that are linked through a communications network. In a distributed cloud computing environment, program modules may be located in both local and remote computer system storage media including memory storage devices.

The technology discussed herein refers to computer-based systems and actions taken by, and information sent to and from, computer-based systems. One of ordinary skill in the art will recognize that the inherent flexibility of computer-based systems allows for a great variety of possible configurations, combinations, and divisions of tasks and functionality between and among components. For instance, processes discussed herein can be implemented using a single computing device or multiple computing devices working in combination. Databases, memory, instructions, and applications can be implemented on a single system or distributed across multiple systems. Distributed components can operate sequentially or in parallel.

Use of language such as "at least one of X, Y, and Z," "at least one of X, Y, or Z," "at least one or more of X, Y, and Z," "at least one or more of X, Y, or Z," "at least one or more of X, Y, and/or Z," or "at least one of X, Y, and/or Z," are intended to be inclusive of both a single item (e.g., just X, or just Y, or just Z) and multiple items (e.g., {X and Y}, {X and Z}, {Y and Z}, or {X, Y, and Z}). The phrase "at least one of" and similar phrases are not intended to convey a requirement that each possible item must be present, although each possible item may be present.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure. For example, unless otherwise explicitly indicated, the steps of a process or method may be performed in an order other than the example embodiments discussed above. Likewise, unless otherwise indicated, various components may be omitted, substituted, or arranged in a configuration other than the example embodiments discussed above.

Further aspects of the present disclosure are provided by the subject matter of the following clauses.

A system, comprising: At least one sensor configured to measure heart rate and heart rate variability (HRV) of a person; at least one activity sensor to measure movement in at least 3-axes; a user interface; at least one processor; anon-transitory computer-readable storage medium with instructions that, when executed by the at least one processor, cause the processor to: receive measurements of heart rate, activity and HRV from the sensor; execute a trained model to determine the person's arousal state based on HRV, activity and heart rate measurements; and provide an indication of the arousal state through the user interface.

A system, comprising: a semi-rigid flexible sensor array neck band which is placed around the users neck and contains (a) multiple array of ECG sensors for detecting the users electrocardiogram from which heart rate variability, heart rate (in Beats Per Minute (BPM)) are measured, (b) $SpO_2$ sensor for detecting and measuring the users oxygen saturation and pulse rate, (c) temperature sensor for measuring the users skin temperature, (d) activity tracker and (e) one or more vibrational motion output emitters which emits vibration; an embedded signal processor for deriving the vital sign data from the vital sign sensors; an embedded wireless blue-tooth transceiver for (a) transmitting data to the smart phone machine learning/AI processing and (b) for receiving control data from the smart phone machine learning/AI processing unit; a rechargeable battery which can be connected to a standard Universal Serial Bus (USB) charger via USB cable. The rechargeable battery can remain within the neck band and connected to a USB charger and/or can be removed from the neck band for recharging; a user Interface software controller embedded within the smart neck band which is controlled via the software app residing within the smart phone. The user interfaces with the user interface controls displayed on the smartphone touch screen; a software app residing within the smart phone which provides Machine Learning and AI algorithms for (a) automatically identifying the users state condition, (b) manual override mode which allows the user to select their state condition from an embedded database of state conditions, (c) vibratory database for selection of appropriate vibration signal patterns which are transmitted to the vibratory emitters embedded within the neck band via wireless blue-tooth, (d) auditory database which contains a database of infrasound patterns and music which are wirelessly communicated via blue-tooth to wearable ear buds and or headphones.

The system of any preceding clause, further comprising: at least one sensor configured to measure heart rate and heart rate variability (HRV) of a person.

The system of any preceding clause, further comprising: at least one vibrational motion output emitter in direct contact with the skin of the person.

The system of any preceding clause, wherein the vibrational motion output emitter is within a predefined distance of sensory pathways communicating with the nucleus of the solitary tract and the ventral vagal complex.

The system of any preceding clause, further comprising: At least one acoustic output emitter, wherein the acoustic output emitter provides auditory stimuli to the person.

The system of any preceding clause, further comprising: at least one vibrational motion output emitter and at least one acoustic output emitter, wherein the acoustic and vibrational stimuli are synchronized to enhance the neural regulation of the autonomic nervous system.

The system of any preceding clause, wherein the storage medium further includes instructions to: compare HRV, heart rate, movement, and body posture measurements to previously collected data; initiate a treatment by applying vibratory motion to the skin near sensory pathways influencing the ANS; and perform at least one of: adjust the stimulation pattern to enhance activity of the parasympathetic nervous system or adjust the stimulation pattern to inhibit activity of the calming parasympathetic nervous system to enhance performance.

The system of any preceding clause, wherein the storage medium further includes instructions to: compare HRV and heart rate measurements to previously collected data; identify and propose a treatment through the user interface; initiate the treatment upon user authorization.

The system of any preceding clause, wherein the storage medium further includes instructions to: receive a user-selected arousal state; and initiate vibratory motion to influence the ANS according to the selected state.

The system of any preceding clause, further comprising a band configured to couple to a portion of the person's body, with sensors and vibrational motion emitters located on the band.

The system of any preceding clause, wherein the band couples to the neck of the person.

The system of any preceding clause, wherein the user interface is located on a separate computing device.

The system of any preceding clause, wherein the band and the computing device communicate wirelessly.

The system of any preceding clause, wherein the storage medium further includes instructions to: use accelerometer data to differentiate between seated, standing, and walking HRV measurements; and adjust interventions based on the user's activity.

The system of any preceding clause, wherein the sensors employ a unique method for collecting ECG data to improve accuracy.

The system of any preceding clause, wherein the storage medium further includes instructions to: record HRV changes and stimulation parameters; and compare the user's HRV history and stimulus responses to optimize treatment parameters.

A method comprising: receiving HRV, movement and heart rate measurements from at least one sensor; executing a trained model to determine the person's arousal state; and indicating the arousal state through a user interface.

The method of any preceding clause, further comprising: comparing current measurements to historical data; and initiating vibratory motion treatment and/or auditory stimuli to regulate the ANS.

The method of any preceding clause, further comprising: comparing measurements to historical data; and proposing a treatment through the user interface and initiating it upon user authorization.

The method of any preceding clause, further comprising: receiving a user-selected arousal state; and initiating vibratory motion treatment and/or auditory stimuli based on the selection.

The method of any preceding clause, wherein sensors and vibrational motion emitters are located on a band configured to couple to the person.

The method of any preceding clause, wherein the band couples to the neck of the person.

The method of any preceding clause, wherein the user interface is on a separate computing device.

The method of any preceding clause, wherein the band and computing device communicate wirelessly.

The method of any preceding clause, further comprising: providing auditory stimuli through at least one acoustic output emitter to influence the ANS.

The method of any preceding clause, further comprising: providing synchronized auditory and vibratory stimuli to enhance the regulation of the ANS.

The method of any preceding clause, wherein executing the trained model comprises use of a machine learning or other advanced signal processing method.

The method of any preceding clause, further comprising: isolating a consistent Electrocardiogram (ECG) complex within noisy electrophysiological recordings.

The method of any preceding clause, wherein isolating of the consistent ECG complex within the noisy electrophysiological recordings comprises independent components analysis (ICA) or another method for transforming the independent channels of electrophysiological data.

The method of any preceding clause, wherein the ICA isolates the consistent ECG complex from additional known sources of electrophysiological activity in the measurement location, such as electromyographic (EMG) signals from muscles in the body region.

The method of any preceding clause, wherein the ICA (or other machine learning method) is optimized to isolate the ECG complex into one of several extracted components.

The method of any preceding clause, wherein the ICA re-calibrates the ECG extraction while the ECG extraction is ongoing, thereby providing continuous ECG data to a HRV extraction algorithm.

The method of any preceding clause, wherein the ICA comprises optimization of the ICA through calibration steps taken by the user, either under direction from an app or through automated detection of calibration activities.

The method of any preceding clause, wherein the calibration activities for optimizing the ICA comprise generation of known noise sources, such as movement of the body in the region of the ECG sensor.

A system, comprising: at least one physiological sensor configured to measure heart rate and heart rate variability (HRV) of a person; at least one accelerometer; at least one emitter; at least one processor; a non-transitory computer-readable storage medium with instructions that, when executed by the at least one processor, cause the at least one processor to: receive measurements from the at least one physiological sensor and the at least one accelerometer; execute a trained model based on the measurements, wherein input to the trained model comprises the measurements and output of the trained model comprises a current user state; and causing the at least one emitter to generate output based on the current user state, the output comprising at least one of vibrational output or acoustic output.

The system of any preceding clause, wherein the at least one emitter is in direct contact with skin of the person.

The system of any preceding clause, wherein the at least one emitter is within a predefined distance 15 mm of sensory pathways communicating with a nucleus of the solitary tract and the ventral vagal complex of the person.

The system of any preceding clause, further comprising: a band, wherein the band is configured to couple to a portion of the person's body, and wherein the at least one physiological sensor and the at least one accelerometer are integrated into the band.

The system of any preceding clause, wherein the band couples to the neck of the person.

The system of any preceding clause, wherein: the output comprises both the vibrational output and the acoustic output; and the vibrational output and the acoustic output are synchronized.

The system of any preceding clause, the non-transitory computer-readable storage medium having additional instructions stored that, when executed by the at least one processor, cause the processor to: generate, based on the measurements: a Heart Rate Variability (HRV) of the person; and a heart rate of the person; and compare the HRV and the heart rate of the person against historical data of the person, resulting in a comparison, wherein the output is further based on the comparison.

The system of any preceding clause, wherein the output enhances activity of the parasympathetic nervous system of the person.

The system of any preceding clause, wherein the output inhibits activity of the parasympathetic nervous system of the person The system of any preceding clause, wherein the non-transitory computer-readable storage medium has additional instructions stored that, when executed by the at least one processor, cause the processor to perform operations comprising: prior to the causing of the at least one emitter to generate the output: comparing the measurements against historical data of the person, resulting in a comparison; identifying, based on the comparison, a proposed treatment; communicating, via a user interface, the proposed treatment to the person; and upon receiving, via the user interface, authorization from the person, initiating the proposed treatment, resulting in the output.

The system of any preceding clause, wherein the non-transitory computer-readable storage medium has additional instructions stored that, when executed by the at least one processor, cause the processor to perform operations comprising: prior to the causing of the at least one emitter to generate the output: receiving, from the person via a user interface, a user-selected desired state; and generating a planned stimulation to take the person from the current user state to the user-selected desired state, wherein the output is generated according to the planned stimulation.

A method comprising: receiving, at a computer system from at least one physiological sensor and from at least one accelerometer, measurements of a user, the at least one physiological sensor and the at least one accelerometer embedded within a neck band worn by the user; executing, via at least one processor of the computer system, a trained model, wherein inputs to the trained model comprise the measurements, and wherein output of the trained model comprise a current user state; and displaying, via a user interface of the computer system, the current user state.

The method of any preceding clause, further comprising: comparing, via the at least one processor, the measurements against historical data of the user, resulting in a comparison; identifying, via the at least one processor, a vibroacoustic stimulation pattern appropriate for the user based on the comparison; and transmitting, from the computer system to the neck band, instructions to begin the vibroacoustic stimulation pattern.

The method of any preceding clause, further comprising: comparing, via the at least one processor, the measurements against historical data of the user, resulting in a comparison; identifying, via the at least one processor, a vibroacoustic stimulation pattern appropriate for the user based on the comparison; proposing the vibroacoustic stimulation pattern to the user via the user interface of the computer system; receiving, via the user interface, authorization from the user to begin the vibroacoustic stimulation pattern; and after receiving the authorization, transmitting, from the computer system to the neck band, instructions to begin the vibroacoustic stimulation pattern.

The method of any preceding clause, further comprising: receiving, from the user via the user interface of the computing system, a user-desired state; generating, via the at least one processor, a stimulation plan to bring the user from the current user state to the user-desired state; and transmitting, from the computing system to the neck band, instructions to begin generating vibroacoustic stimulation according to the stimulation plan.

The method of any preceding clause, wherein the computing system comprises at least one of a smart phone or a tablet computer.

The method of any preceding clause, wherein the neck band and the computing system communicate wirelessly.

The method of any preceding clause, further comprising: transmitting, from the computing system to the neck band, instructions to begin generating vibroacoustic stimulation based on the current user state.

The method of any preceding clause, wherein the current user state is associated with stress, and the vibroacoustic stimulation is selected to reduce the stress.

A non-transitory computer-readable storage medium having instructions stored which, when executed by at least one processor, cause the at least one processor to perform operations comprising: receiving, from at least one physiological sensor and from at least one accelerometer, measurements of a user, the at least one physiological sensor and the at least one accelerometer embedded within a neck band worn by the user; executing a trained model, wherein inputs to the trained model comprise the measurements, and wherein output of the trained model comprise a current user state; and causing display, via a user interface, of the current user state.

We claim:

1. A system, comprising:

at least one physiological sensor configured to measure heart rate and heart rate variability (HRV) of a person;

at least one accelerometer;

at least one emitter;
at least one processor;
a non-transitory computer-readable storage medium with instructions that, when executed by the at least one processor, cause the at least one processor to:
receive measurements from the at least one physiological sensor and the at least one accelerometer;
execute a trained model based on the measurements, wherein input to the trained model comprises the measurements and output of the trained model comprises a current user state; and
causing the at least one emitter to generate output based on the current user state, the output comprising at least one of vibrational output or acoustic output,
variably modulating the output across a frequency range within a stimulation window, wherein during the stimulation window a size of the frequency range decreases and a cycle time between modulation decreases until a maximized response is identified,
wherein while the at least one emitter generates the output the at least one processor executes a dual feedback loop comprising an outside feedback loop and an inside feedback loop,
the outside loop monitoring the measurements and initiating stimulations, and
the inside loop personalizing the output to the person based on physiological reactions to the output, wherein the inside loop is only active while the output is being generated, the inner loop identifying the maximized response.

2. The system of claim 1, wherein the at least one emitter is in direct contact with skin of the person.

3. The system of claim 1, wherein the at least one emitter is configured to be positioned on the neck of the person over a carotid sinus region while generating the output, thereby enabling mechanical stimulation of carotid baroreceptors via vibroacoustic energy.

4. The system of claim 3, further comprising:
a band,
wherein the band is configured to couple to a portion of the person's body, and
wherein the at least one physiological sensor and the at least one accelerometer are integrated into the band.

5. The system of claim 4, wherein the band is configured to couple to the neck of the person.

6. The system of claim 1, wherein:
the output comprises both the vibrational output and the acoustic output;
the vibrational output and the acoustic output are synchronized;
the at least one emitter comprises at least two emitters, wherein the output of each emitter in the at least two emitters is asynchronous with respect to other emitters within the at least two emitters, such that the output of each emitter does not overlap with output from another emitter within the at least two emitters.

7. The system of claim 1, the non-transitory computer-readable storage medium having additional instructions stored that, when executed by the at least one processor, cause the processor to:
generate, based on the measurements:
the Heart Rate Variability (HRV) of the person; and
the heart rate of the person; and
compare the HRV and the heart rate of the person against historical data of the person, resulting in a comparison, wherein the output is further based on the comparison.

8. The system of claim 1, wherein the output enhances activity of the parasympathetic nervous system of the person.

9. The system of claim 1, wherein the output inhibits activity of the parasympathetic nervous system of the person.

10. The system of claim 1, wherein the non-transitory computer-readable storage medium has additional instructions stored that, when executed by the at least one processor, cause the processor to perform operations comprising:
prior to the causing of the at least one emitter to generate the output:
comparing the measurements against historical data of the person, resulting in a comparison;
identifying, based on the comparison, a proposed treatment;
communicating, via a user interface, the proposed treatment to the person; and
upon receiving, via the user interface, authorization from the person, initiating the proposed treatment, resulting in the output,
wherein a center frequency of the frequency range for modulating the output varies while the inner loop identifies the maximized response.

11. The system of claim 1, wherein the non-transitory computer-readable storage medium has additional instructions stored that, when executed by the at least one processor, cause the processor to perform operations comprising:
prior to the causing of the at least one emitter to generate the output:
receiving, from the person via a user interface, a user-selected desired state; and
generating a planned stimulation to take the person from the current user state to the user-selected desired state,
wherein the output is generated according to the planned stimulation.

12. A method comprising:
receiving, at a computer system from at least one physiological sensor and from at least one accelerometer, measurements of a user, the at least one physiological sensor and the at least one accelerometer embedded within a neck band worn by the user;
executing, via at least one processor of the computer system, a trained model, wherein inputs to the trained model comprise the measurements, and wherein output of the trained model comprise a current user state;
displaying, via a user interface of the computer system, the current user state;
comparing, via the at least one processor, the measurements against historical data of the user, resulting in a comparison;
identifying, via the at least one processor, a vibroacoustic stimulation pattern appropriate for the user based on the comparison; and
transmitting, from the computer system to the neck band, instructions to begin generating output via at least two emitters based on the vibroacoustic stimulation pattern,
variably modulating the output across a frequency range within a stimulation window, wherein during the stimulation window a size of the frequency range decreases and a cycle time between modulation decreases until a maximized response is identified,
wherein the output of each emitter in the at least two emitters is asynchronous with respect to other emitters within the at least two emitters, such that the output of each emitter does not overlap with output from another emitter within the at least two emitters, wherein while the at least two emitters generate the output the at least one processor executes a dual feedback loop comprising an outside feedback loop and an inside feedback loop, the outside loop monitoring the measurements and initiating stimulations, and the inside loop personalizing the output to the person based on physiological reactions to the output, wherein the inside loop is only active while the output is being generated, the inner loop identifying the maximized response.

13. The method of claim 12, further comprising:

comparing, via the at least one processor, the measurements against historical data of the user, resulting in a comparison;

identifying, via the at least one processor, a vibroacoustic stimulation pattern appropriate for the user based on the comparison;

proposing the vibroacoustic stimulation pattern to the user via the user interface of the computer system;

receiving, via the user interface, authorization from the user to begin the vibroacoustic stimulation pattern; and after receiving the authorization, transmitting, from the computer system to the neck band, instructions to begin the vibroacoustic stimulation pattern.

14. The method of claim 12, further comprising:

receiving, from the user via the user interface of the computing system, a user-desired state;

generating, via the at least one processor, a stimulation plan to bring the user from the current user state to the user-desired state; and transmitting, from the computing system to the neck band, instructions to begin generating vibroacoustic stimulation according to the stimulation plan.

15. The method of claim 12, wherein the computing system comprises at least one of a smart phone or a tablet computer.

16. The method of claim 12, wherein the neck band and the computing system communicate wirelessly.

17. The method of claim 12, further comprising:

transmitting, from the computing system to the neck band, instructions to begin generating vibroacoustic stimulation based on the current user state.

18. The method of claim 17, wherein the current user state is associated with stress, and the vibroacoustic stimulation is selected to reduce the stress.

19. A non-transitory computer-readable storage medium having instructions stored which, when executed by at least one processor, cause the at least one processor to perform operations comprising:

receiving, from at least one physiological sensor and from at least one accelerometer, measurements of a user, the at least one physiological sensor and the at least one accelerometer embedded within a neck band worn by the user;

executing a trained model, wherein inputs to the trained model comprise the measurements, and wherein output of the trained model comprise a current user state;

causing display, via a user interface, of the current user state;

comparing the measurements against historical data of the user, resulting in a comparison;

identifying a vibroacoustic stimulation pattern appropriate for the user based on the comparison; and transmitting, from the at least one processor to the neck band, instructions to begin generating output via at least one emitter based on the vibroacoustic stimulation pattern, variably modulating the output across a frequency range within a stimulation window, wherein during the stimulation window a size of the frequency range decreases and a cycle time between modulation decreases until a maximized response is identified, wherein while the at least one emitter generates the output the at least one processor executes a dual feedback loop comprising an outside feedback loop and an inside feedback loop, the outside loop monitoring the measurements and initiating stimulations, and the inside loop personalizing the output to the person based on physiological reactions to the output, wherein the inside loop is only active while the output is being generated, the inner loop identifying the maximized response.

20. The method of claim 12, wherein the vibroacoustic stimulation pattern comprises a carrier frequency in a range of 30 Hz to 120 Hz, amplitude-modulated in a cyclical pattern, wherein a timing or duration of the output is based on a physiological cycle detected by the at least one physiological sensor.

* * * * *